(12) United States Patent
Qian et al.

(10) Patent No.: US 11,944,721 B2
(45) Date of Patent: Apr. 2, 2024

(54) NERVE CONDUIT LOADED WITH ADIPOSE-DERIVED STEM CELLS AND PREPARATION METHOD THEREOF

(71) Applicant: Shanghai Sixth People's Hospital, Shanghai (CN)

(72) Inventors: Yun Qian, Shanghai (CN); Cunyi Fan, Shanghai (CN); Xiangyun Yao, Shanghai (CN); Zhiwen Yan, Shanghai (CN); Lingchi Kong, Shanghai (CN); Xu Wang, Shanghai (CN)

(73) Assignee: SHANGHAI SIXTH PEOPLE'S HOSPITAL, Shanghai (CN)

( * ) Notice: Subject to any disclaimer, the term of this patent is extended or adjusted under 35 U.S.C. 154(b) by 0 days.

(21) Appl. No.: 18/305,346

(22) Filed: Apr. 22, 2023

(65) Prior Publication Data

US 2023/0321321 A1 Oct. 12, 2023

Related U.S. Application Data

(63) Continuation of application No. PCT/CN2023/079721, filed on Mar. 6, 2023.

(30) Foreign Application Priority Data

Mar. 30, 2022 (CN) .......................... 202210327300.5

(51) Int. Cl.
  *A61L 27/38* (2006.01)
  *A61L 27/44* (2006.01)
(52) U.S. Cl.
  CPC ......... *A61L 27/3878* (2013.01); *A61L 27/383* (2013.01); *A61L 27/443* (2013.01); *A61L 2430/32* (2013.01)

(58) Field of Classification Search
  None
  See application file for complete search history.

(56) References Cited

U.S. PATENT DOCUMENTS

2010/0168870 A1* 7/2010 Swain ............... A61F 13/00068
623/23.72

FOREIGN PATENT DOCUMENTS

WO        2016192733 A1    12/2016
WO   WO-2016192733 A1 *  12/2016  ........... A61L 27/227

OTHER PUBLICATIONS

Vijayavenkataraman et al. "3D-Printed PCL/rGO Conductive Scaffolds for Peripheral Nerve Injury Repair". Artif Organs, 2018, 43: 515-523. (Year: 2018).*

(Continued)

*Primary Examiner* — Carlos A Azpuru
*Assistant Examiner* — Casey S Hagopian
(74) *Attorney, Agent, or Firm* — Zhigang Ma

(57) ABSTRACT

A nerve conduit loaded with adipose-derived stem cells and a preparation method thereof are provided. The preparation method includes: S1, adding polycaprolactone and polyvinylpyrrolidone into a binary organic solvent, performing ultrasonic treatment, and then adding reduced graphene oxide nanoparticles to obtain a spinning solution; S2, electrospinning with the spinning solution and then washing for several times to obtain a semi-finished conduit product; and S3, injecting a cell mixture into the semi-finished conduit product to obtain the nerve conduit. A fiber surface of the nerve conduit has groove structures, and thus a specific surface area and cell adhesion sites are increased, and adhesion and proliferation of cells are facilitated. By loading the adipose-derived stem cells, neurotrophic phenotypic effect of peripheral nerve scaffold is improved, and can effectively avoid immunological rejection of transplanta- (Continued)

tion, promote orientational growth of axons into the nerve conduit and promote myelination effect of Schwann cells.

6 Claims, 3 Drawing Sheets

(56)  References Cited

OTHER PUBLICATIONS

Mobasseri et al. "Polymer scaffolds with preferential parallel grooves enhance nerve regeneration", Tissue Eng Part A, Mar. 1, 2015, 21(506): 1152-2262. (Year: 2015).*
Sanjairaj Vijayavenkataman et al., "3D-Printed PCL/rGO Conductive Scaffolds for Peripheral Nerve Injury Repair", Artificial Organs, 2019, pp. 515-523, vol. 43, No. 5.
Lai Ming-he et al., "Properties of Hydrophilicity/Hydrophobicity and Biodegradation of Polycaprolactone/Polyvinylpyrrodidone Blends", Synthetic Fiber in China, 2011, pp. 22-26, vol. 40(10).
CNIPA, Notification of a First Office Action for CN202210327300.5, dated Sep. 15, 2022.
Shanghai Sixth People's Hospital (Applicant), Reply to Notification of a First Office Action for CN202210327300.5, w/replacement claims, dated Nov. 15, 2022.
Shanghai Sixth People's Hospital (Applicant), Supplemental (allowed) replacement claims, Dec. 8, 2022.
CNIPA, Notification to grant patent right for invention in CN202210327300.5, dated Dec. 26, 2022.

* cited by examiner

NERVE CONDUIT LOADED WITH ADIPOSE-DERIVED STEM CELLS AND PREPARATION METHOD THEREOF

TECHNICAL FIELD

The invention relates to the field of electrospinning scaffolds, and particularly to a nerve conduit loaded with adipose-derived stem cells and a preparation method thereof.

BACKGROUND

Peripheral nerve injury is a refractory disease with high incidence in clinic. Long-segment peripheral nerve injury often leads to low repair efficiency due to mismatching of nerve stumps and a slow growth rate, resulting in motor and sensory dysfunction of a patient, and even deformity and disability in severe cases. For small defects, peripheral nerves have certain regenerative ability and can repair the defects by themselves, which can be treated by nerve stump anastomosis in clinic. Treatment of long-segment peripheral nerve defects is quite challenging, and at present, a gold standard in clinic is still nerve transplantation, but this treatment has some important defects, such as donor limitation, size mismatch and donor site damage, and long-term follow-up found that functional recovery of patients after treatment is very limited, which greatly limits its wide clinical application. With the development and improvement of tissue engineering products, the role of nerve conduit bridging method in clinical treatment has been continuously increased. By efficiently imitating a structure and a function of peripheral nerve tissue, various functionalized nerve conduits are potential to replace autologous nerve transplantation and become the first choice for clinical treatment.

Nowadays, there are some improved designs in products and inventions of nerve conduits at home and abroad, which not only can bridge stumps of nerve and provide an appropriate mechanical support for peripheral nerve regeneration, but also can guide axons to grow into distal ends through orientated micro-nano structure design or inductive bioactive factors, to achieve orientational regeneration of peripheral nerves. However, these bioactive factors with chemotactic induction loaded on nerve conduits not only have uncertain effects, but also are prone to rapid degradation after implantation and have the risk of liver and kidney toxicity and tumor gene mutation. Compared with biochemical preparations, physical signal regulation has characteristics of exact and stable effect, sustained effecting and safe application in vivo, which can make up for shortcomings of the biochemical preparations and have a higher application prospect. Imitating orientated structures and fiber morphologies of peripheral nerves has been proved to have the effect of chemotactic regenerative axons directionally growing into distal ends, which is of great significance for long-segment peripheral nerve defects (more than 10 mm). However, relying only on adjustment of a topological structure of nerve conduit cannot change the fact that nerve regeneration is slow and thus cannot achieve efficient regeneration after nerve injury.

In addition to the topological structure, many physical signal stimuli can regulate cell phenotype changes and accelerate nerve regeneration, including physical stimuli such as electricity, magnetism, light and ultrasound. Peripheral nerve tissue has good electrical activity, and there are widespread bioelectrical phenomena, and thus it is a common and effective clinical treatment to use conductive implant materials to promote repairs of electrically active tissue. Polycaprolactone (PCL) can be used as a carrier of conductive particles to provide electrical stimulation sites to stimulate bioelectric transmission from proximal to distal and promote regenerative signaling. Although dual-stimulation of orientated structure and electrical signal can promote cell proliferation and migration at the cellular level, Schwann cells cannot rapidly proliferate or migrate to a repair site of severe peripheral nerve injury in a short period of time, which makes the functionalized nerve conduit unable to play a role at the cellular level.

As one of the three major elements of tissue engineering, cells can further exert the efficacy of bionic grafts. Mesenchymal stem cells have strong abilities of amplification and differentiation, and can differentiate into Schwann cells under specific culture conditions in vitro. Adipose-derived mesenchymal stem cells (ADMSCs) are seed cells commonly used in clinical stem cell transplantation, which not only have the ability of proliferation and multi-directional differentiation, but also can make up for the shortage of Schwann cells and avoid the immunological rejection caused by allogeneic transplantation, and thus have high clinical transformation potential. However, the multi-element combination of the adipose-derived stem cell, the conductive material and the orientated nerve conduit is a huge problem in terms of design.

Although current tissue engineering nerve scaffold materials can achieve orientated topological structure and provide continuous and effective electrical signal stimulation to induce the growth, migration and arrangement of Schwann cells, the regenerative repair ability of Schwann cell is low in long-segment peripheral nerve injury, and an effect of material-cell interface is not significant, which can not realize a remodeling of nerve tissue structure. At present, the research of nerve conduits mainly focuses on topological structures applied to conductive nanoparticles or fibers alone, and the research of combining the two with stem cell transplantation is even less. It is difficult to achieve both good conductivity and cell activity after transplantation in vivo.

Therefore, there is an urgent need of a nerve conduit that can combine a topological structure with conductive nanoparticles to construct a dual bionic peripheral nerve microenvironment and achieve multi-angle bionic effect by loading adipose-derived stem cells on the premise of ensuring biological safety.

SUMMARY

Aiming at the shortcomings in the prior art, purposes of the invention are to provide a nerve conduit loaded with adipose-derived stem cells and a preparation method thereof.

To achieve the above purposes, technical solutions of embodiments of the invention are as follows.

Specifically, in a first aspect, an embodiment of the invention provides a preparation method of a nerve conduit loaded with adipose-derived stem cells, including steps:
S1, adding polycaprolactone and polyvinylpyrrolidone into a binary organic solvent, performing ultrasonic treatment, and then adding reduced graphene oxide nanoparticles to obtain a spinning solution;
S2, electrospinning with the spinning solution obtained in the S1, and then washing for several times to obtain a semi-finished conduit product; and
S3, injecting a cell mixture into the semi-finished conduit product obtained in the S2 to obtain the nerve conduit.

In an embodiment, in the S1, the binary organic solvent is organic solvents of dichloromethane and dimethylformamide, and a volume ratio of the dichloromethane to the dimethylformamide is (2~4):1.

In an embodiment, in the S1, time of the performing ultrasonic treatment is 20~40 minutes.

In an embodiment, in the S2, the electrospinning includes: the spinning solution is added into a syringe, a receiving distance of a receiving bar is 10 cm~20 cm, a rotational speed of the receiving bar is 5 rpm~15 rpm, a voltage of 10 kV~20 kV is applied (for generation of an electric field), a speed of a propelling pump is 2 mL/h~3 mL/h, and a negative voltage applied between two ends of an insulating bar is −2 kV~−1 kV.

In an embodiment, in the S2, a detergent used for the washing comprises alcohol and/or water.

In an embodiment, in the S3, a density of adipose-derived mesenchymal stem cells in the cell mixture is $10^6$/mL~$10^8$/mL.

In an embodiment, the cell mixture further includes a substance capable of enabling the cell mixture to be cured.

In an embodiment, the cell mixture specifically further includes Matrigel.

In an embodiment, the cell mixture specifically further includes fibrinogen-thrombin.

In an embodiment, in the S3, an injection ratio of the cell mixture to the semi-finished conduit product is 100 μL/cm~200 μL/cm.

In a second aspect, an embodiment of the invention provides a nerve conduit loaded with adipose-derived stem cells prepared by the preparation method according to any one of the above embodiments.

In an embodiment, a length of the nerve conduit is 1 cm~2 cm, an inner diameter of the nerve conduit is 2 mm~4 mm, and a wall thickness of the nerve conduit is 0.4 mm~0.45 mm.

The above technical solutions of the invention, compared with the prior art, may achieve beneficial effects as follows.
(1) The invention can improve the neurotrophic phenotype effect of a peripheral nerve scaffold by loading adipose-derived stem cells, and meanwhile, the adipose-derived stem cells can effectively avoid an immunological rejection of transplantation, can promote an orientational growth of axons into the nerve conduit and promote myelinization effect of Schwann cells.
(2) A fiber surface of the nerve conduit loaded with adipose-derived stem cells according to the invention have groove structures, which can increase a specific surface area and cell adhesion sites, and thus is beneficial to adhesion and proliferation of cells; and meanwhile, a peripheral nerve microenvironment can promote orientational differentiation of the adipose-derived mesenchymal stem cells in neurogenic direction, and promote the stem cells to secrete more neurotrophic factors (GDNF, NGF and the like), thereby improving the migration and growth of supporting cells (Schwann cells and vascular endothelial cells), and accelerating the repair and regeneration of nerve defects.
(3) The nerve conduit loaded with adipose-derived stem cells according to the invention is added with the reduced graphene oxide nanoparticles, which can respond to bioelectric signals in the peripheral nerve microenvironment, promote the neurogenic differentiation of the adipose-derived stem cells, construct cell bioelectric signal intelligent response and cell information feedback, and accelerate repair and regeneration of nerves.

DETAILED DESCRIPTION OF EMBODIMENTS

Technical solutions in embodiments of the invention will be clearly and completely described below in conjunction with the accompanying drawings of the embodiments of the invention. Apparently, the embodiments as described are only some of embodiments of the invention, rather than all of embodiments of the invention. Based on the embodiments as described of the invention, all other embodiments obtained by those skilled in the art without creative work are within the scope of protection of the invention.

It should be noted that the embodiments as described of the invention and features in the embodiments can be combined with each other on the prerequisite of without conflict.

The invention will be further described with reference to the accompanying drawings and specific embodiments, but not as a limitation of the invention.

Embodiment 1

Figure 7:
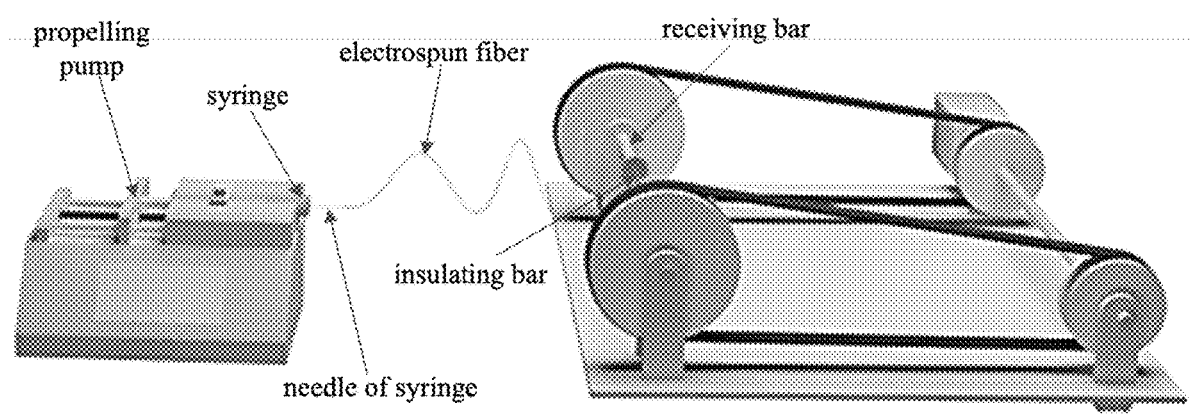
FIG. 7 illustrates a schematic structural view of an electrospinning device.

This embodiment provides a preparation method of a nerve conduit, including steps as follows.
S1, adding 1 gram (g) of polycaprolactone and 0.8 g of polyvinylpyrrolidone into 10 milliliters (mL) of dichloromethane/dimethylformamide organic solvent (a volume ratio of dichloromethane to dimethylformamide is 3:1), performing ultrasonic treatment for 30 minutes, and then adding 2% (w/w, i.e., weight to weight ratio) of reduced graphene oxide nanoparticles to obtain a spinning solution.
S2, adding the spinning solution obtained in the S1 into a syringe, electrospinning under conditions that a receiving distance of a receiving bar is 15 cm (i.e., a distance from the receiving bar to the syringe is 15 cm), a rotational speed of the receiving bar is 10 revolutions per minute (rpm), a voltage of 15 kilovolts (kV) is applied (for generation of an electric field), a speed of a propelling pump (for driving the syringe) is 2.5 milliliter per hour (mL/h), and a negative voltage applied between two ends of an insulating bar is −1.5 kV, and then washing with alcohol and water for three times to remove the polyvinylpyrrolidone and thereby obtain groove structures on a fiber surface, thereby obtaining a semi-finished conduit product. Moreover, FIG. 7 illustrates an electrospinning device including the syringe, the receiving bar, the propelling pump and the insulating bar, and a basic structure thereof is well-known to those skilled in the art and thus will not be described in detail herein. In addition, the voltage of 15 kV is generally applied on a needle of the syringe.

S3, injecting a cell mixture into an inner wall of the semi-finished conduit product obtained in the S2 according to a ratio of 133 microliters per centimeter (L/cm), and curing at a constant temperature of 37 degrees Celsius (° C.) to obtain the nerve conduit. In the cell mixture, a density of adipose-derived mesenchymal stem cells is $10^7$/mL, and the cell mixture further includes Corning Matrigel®.

Embodiment 2

This embodiment provides another preparation method of a nerve conduit, including steps as follows.

S1, adding 1 g of polycaprolactone and 0.4 g of polyvinylpyrrolidone into 10 mL of dichloromethane/dimethylformamide organic solvent (a volume ratio of dichloromethane to dimethylformamide is 3:1), performing ultrasonic treatment for 20 minutes, and then adding 1% (w/w) of reduced graphene oxide nanoparticles to obtain a spinning solution.

S2, adding the spinning solution obtained in the S1 into a syringe, electrospinning under conditions that a receiving distance of a receiving bar is 15 cm, a rotational speed of the receiving bar is 10 rpm, a voltage of 15 kV is applied, a speed of a propelling pump is 2.5 mL/h, and a negative voltage applied between two ends of an insulating bar is −1.5 kV, and then washing with alcohol and water for three times to remove the polyvinylpyrrolidone and thereby obtain groove structures on a fiber surface, thereby obtaining a semi-finished conduit product.

S3, injecting a cell mixture into an inner wall of the semi-finished conduit product obtained in the S2 according to a ratio of 105 µL/cm, and curing by ultraviolet light illumination for 5 minutes to obtain the nerve conduit. In the cell mixture, a density of adipose-derived mesenchymal stem cells is $10^7$/mL, and the cell mixture further includes 1% (wt %) of GrowDex® hydrogel.

Embodiment 3

This embodiment provides still another preparation method of a nerve conduit, including steps as follows.

S1, adding 1.2 g of polycaprolactone and 0.8 g of polyvinylpyrrolidone into 10 mL of dichloromethane/dimethylformamide organic solvent (a volume ratio of dichloromethane to dimethylformamide is 3:1), performing ultrasonic treatment for 40 minutes, and then adding 2.5% (w/w) of reduced graphene oxide nanoparticles to obtain a spinning solution.

S2, adding the spinning solution obtained in the S1 into a syringe, electrospinning under conditions that a receiving distance of a receiving bar is 15 cm, a rotational speed of the receiving bar is 10 rpm, a voltage of 15 kV is applied, a speed of a propelling pump is 2.5 mL/h, and a negative voltage applied between two ends of an insulating bar is −1.5 kV, and then washing with alcohol and water for three times to remove the polyvinylpyrrolidone and obtain groove structures on a fiber surface, thereby obtaining a semi-finished conduit product.

S3, injecting a cell mixture into an inner wall of the semi-finished conduit product obtained in the S2 according to a ratio of 133 µL/cm to obtain the nerve conduit. In the cell mixture, a density of adipose-derived mesenchymal stem cells is $10^7$/mL, and the cell mixture further includes fibrinogen-thrombin.

Testing Embodiment

Figure 4:
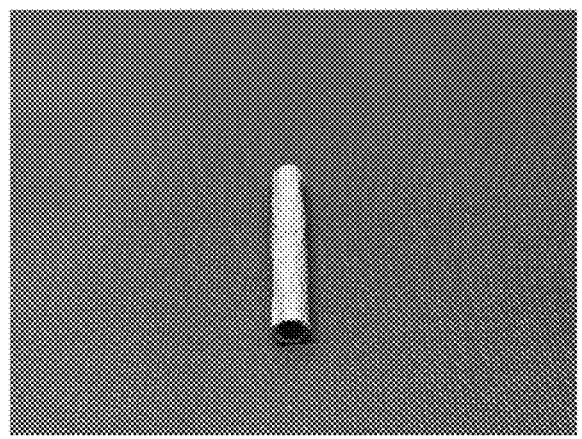
FIG. 4 illustrates a photogram of a nerve conduit.
Figure 5:
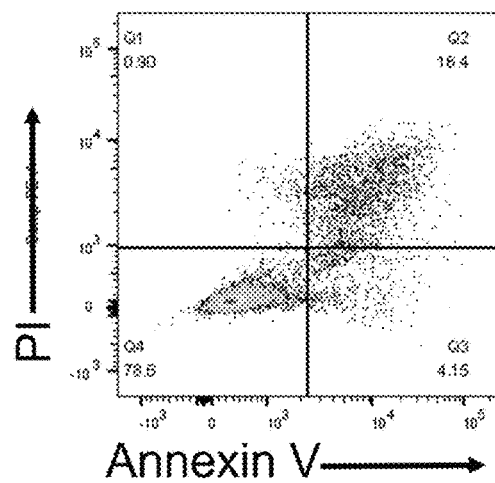
FIG. 5 illustrates a diagram of showing survival of adipose-derived stem cells after being in vitro cultured on a scaffold for 3 days.

The appearance of the nerve conduit obtained in the embodiment 1 was visually observed, and a length, a wall thickness and an inner diameter were measured. As shown in FIG. 4, a result was that the length of the nerve conduit was 1.5 cm, the wall thickness of the nerve conduit was 0.4 mm, and the inner diameter of the nerve conduit was 3 mm.

Figure 1A:
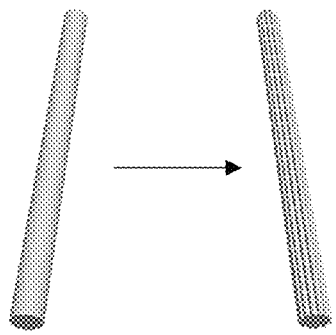
FIG. 1A illustrates a schematic structural diagram of generating grooves on a surface of a nerve conduit.
Figure 1B:
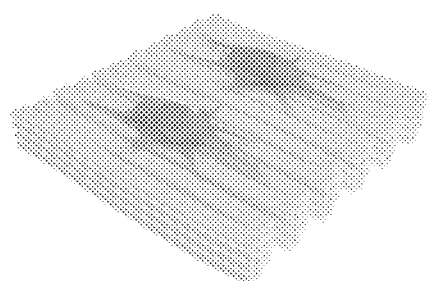
FIG. 1B illustrates a schematic diagram of a cell-fiber scaffold interface.
Figure 2:
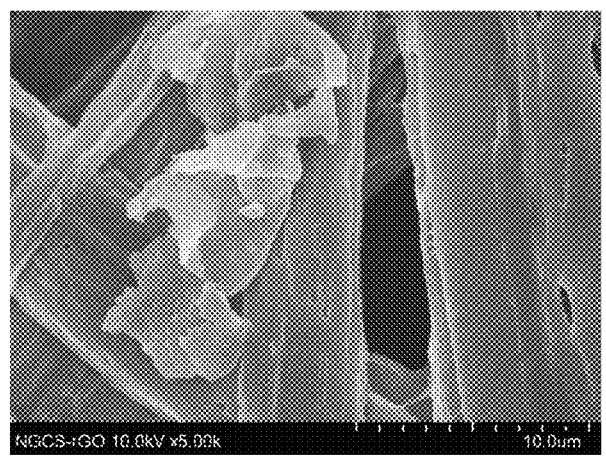
FIG. 2 illustrates a schematic diagram of reduced graphene oxide nanoparticles on surfaces of electrospun fibers.
Figure 3:
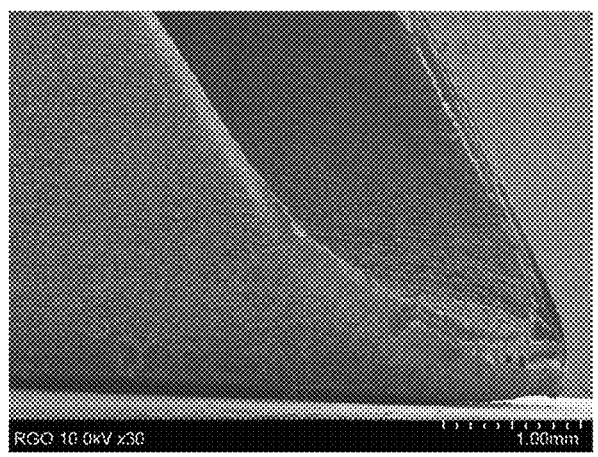
FIG. 3 illustrates a scanning electron microscope (SEM) image of inner and outer layers of a nerve conduit.

The nerve conduit was observed under a scanning electron microscope, and the result is shown in FIGS. 2-3.

Figure 6A:
FIG. 6A illustrates a situation of a scaffold loaded with cells when taken out after being implanted in vivo for 18 weeks.
Figure 6B:
FIG. 6B illustrates a situation of nerve regeneration in the scaffold after being implanted in vivo for 18 weeks.

The nerve conduit was implanted into a nerve defect site in an animal body, and after 18 weeks, it was taken out and cut open for observation. The results are shown in FIGS. 6A and 6B, and nerve growth can be observable in the conduit.

In summary, the illustrated embodiments of the invention improve the neurotrophic phenotype effect of peripheral nerve scaffold by loading adipose-derived stem cells, and meanwhile, the adipose-derived stem cells can effectively avoid an immunological rejection of transplantation, can promote an orientational growth of axons into the nerve conduit and can promote a myelinization effect of Schwann cells. Moreover, a fiber surface of the nerve conduit loaded with adipose-derived stem cells according to the illustrated embodiments of the invention has groove structures, so that a specific surface area and cell adhesion sites are increased, and thus adhesion and proliferation of cells are facilitated; and meanwhile, a peripheral nerve microenvironment can promote adipose orientational differentiation of derived mesenchymal stem cells in neurogenic direction, and promote the stem cells to secrete more neurotrophic factors (GDNF, NGF and the like), thereby improving the migration and growth of supporting cells (Schwann cells and vascular endothelial cells), and accelerating the repair and regeneration of nerve defects. In addition, the nerve conduit loaded with adipose-derived stem cells according to the illustrated embodiments of the invention is added with the reduced graphene oxide nanoparticles, which can respond to bioelectric signals in the peripheral nerve microenvironment, promote the neurogenic differentiation of the adipose-derived stem cells, construct cell bioelectric signal intelligent response and cell information feedback, and accelerate the repair and regeneration of nerves.

The above description is only preferred embodiments of the invention, and is not intended to limit implementations and scope of protection of the invention. For those skilled in the art, it should be appreciated that all equivalent substitutions and obvious changes made based on contents of the specification and the accompanying drawings of the invention should be included in the scope of protection of the invention.

What is claimed is:

1. A preparation method of a nerve conduit loaded with adipose-derived mesenchymal stem cells, comprising:

S1, adding polycaprolactone and polyvinylpyrrolidone into a binary organic solvent, performing ultrasonic treatment, and then adding reduced graphene oxide nanoparticles to obtain a spinning solution;

S2, electrospinning with the spinning solution obtained in the S1, and then washing for several times to obtain a semi-finished conduit product; and S3, injecting a cell mixture comprising adipose-derived mesenchymal stem cells into the semi-finished conduit product obtained in the S2 to obtain the nerve conduit with the adipose-derived mesenchymal stem cells;

wherein the binary organic solvent is organic solvents of dichloromethane and dimethylformamide, and a volume ratio of the dichloromethane to the dimethylformamide is (2-4): 1;

wherein in the S2, the electrospinning comprises: the spinning solution is added into a syringe, a receiving bar has a receiving distance of 10 centimeters (cm)-20 cm and a rotational speed of 5 revolutions per minute (rpm)-15 rpm, a voltage of 10 kilovolts (kV)-20 kV is applied, a speed of a propelling pump is 2 milliliters per hour (mL/h)-3 mL/h, and a negative voltage applied between two ends of an insulating bar is −2 kV--1 kV;

wherein in the S2, a detergent for the washing comprises alcohol and/or water;

wherein a surface of the nerve conduit loaded with adipose-derived stem cells has groove structures.

2. The preparation method according to claim 1, wherein in the S1, time of the performing ultrasonic treatment is 20-40 minutes.

3. The preparation method according to claim 1, wherein in the S3, a density of the adipose-derived mesenchymal stem cells in the cell mixture is $10^6$/mL-$10^8$/mL.

4. The preparation method according to claim 1, wherein in the S3, an injection ratio of the cell mixture to the semi-finished conduit product is 100 microliters per centimeter (μL/cm)-200 μL/cm.

5. The preparation method according to claim 1, wherein the cell mixture further comprises fibrinogen-thrombin.

6. The preparation method according to claim 1, wherein a length of the nerve conduit is 1 cm-2 cm, an inner diameter of the nerve conduit is 2 millimeters (mm)-4 mm, and a wall thickness of the nerve conduit is 0.4 mm-0.45 mm.

* * * * *